United States Patent [19]

Schott

[11] 4,340,816
[45] Jul. 20, 1982

[54] METHOD OF PRODUCING TOMOGRAMS WITH X-RAYS OR SIMILARLY PENETRATING RADIATION

[75] Inventor: Ottfried Schott, Erlangen, Fed. Rep. of Germany

[73] Assignee: Siemens Aktiengesellschaft, Berlin & Munich, Fed. Rep. of Germany

[21] Appl. No.: 58,869

[22] Filed: Jul. 19, 1979

Related U.S. Application Data

[63] Continuation of Ser. No. 837,198, Sep. 28, 1977.

[30] Foreign Application Priority Data

Oct. 19, 1976 [DE] Fed. Rep. of Germany ....... 2647167

[51] Int. Cl.³ ............................................. G03B 41/16
[52] U.S. Cl. ................................ 250/445 T; 250/403; 313/56
[58] Field of Search ...................... 250/445 T; 313/56

[56] References Cited

U.S. PATENT DOCUMENTS 2,667,585  1/1954  Gradstein ...................... 250/445 T
2,905,841  9/1959  Meyer ............................. 313/55
3,250,916  5/1966  Rogers ............................ 313/56
3,389,253  6/1968  Hok ................................. 313/56

Primary Examiner—Craig E. Church
Attorney, Agent, or Firm—Hill, Van Santen, Steadman, Chiara & Simpson

[57] ABSTRACT

In an illustrated embodiment a plurality of radiation sources are arranged to define a scanning path and the sources are successively actuated to produce successively operative beams each of duration sufficient to be recorded, for example by means of a conventional moving photographic cassette. For the case of a linear scan path, an elongated anode may have a succession of continuously energized cathodes, each cathode having an associated blocking screen and being momentarily actuated by removal of the blocking potential. The successive cathodes are actuated in synchronism with the movement of a film cassette, for example, in any suitable manner, or electronic image storage may be utilized in the form of a stationary array of photodetector elements and the required number of arrays of storage units, with electronic sequencing control.

4 Claims, 4 Drawing Figures

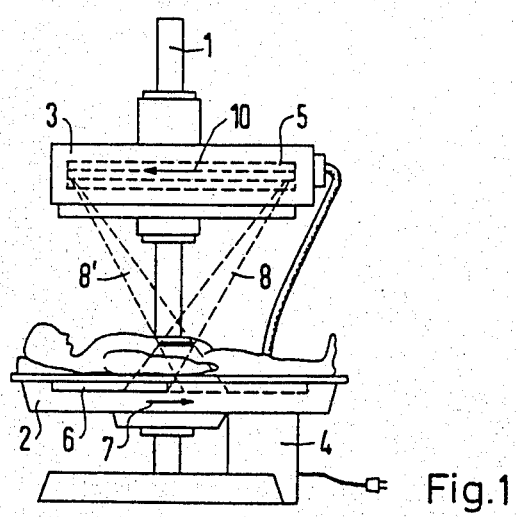
Fig. 1
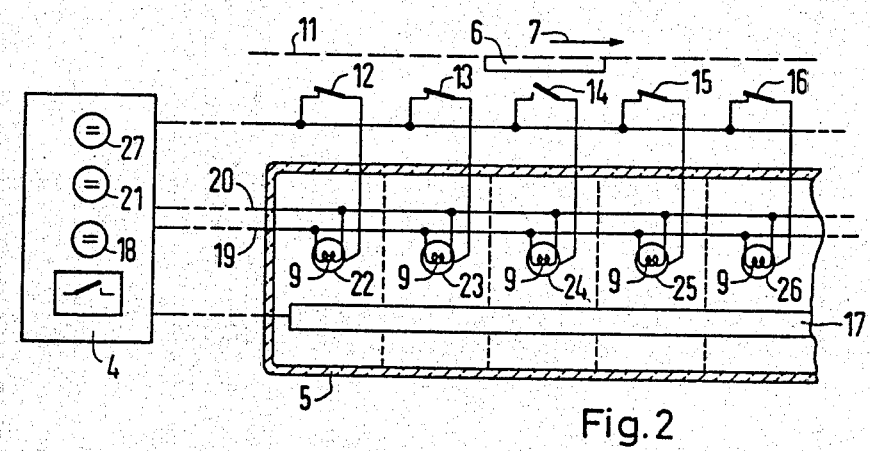
Fig. 2
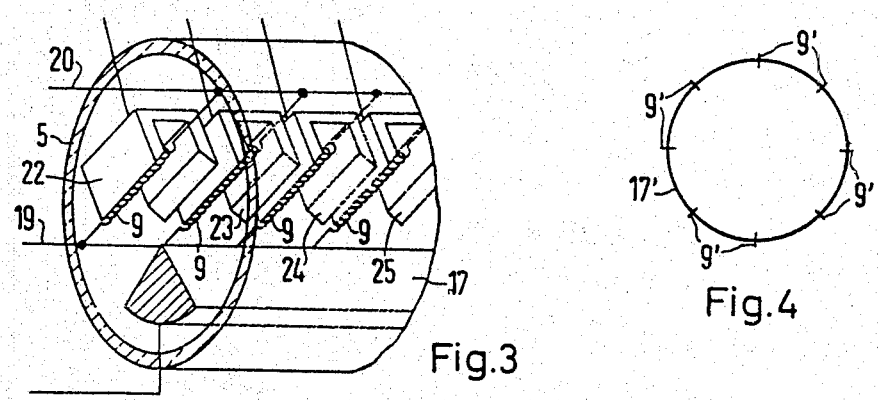
Fig. 3
Fig. 4

METHOD OF PRODUCING TOMOGRAMS WITH X-RAYS OR SIMILARLY PENETRATING RADIATION

This is a continuation, of application Ser. No. 837,198, filed Sept. 28, 1977.

BACKGROUND OF THE INVENTION

Methods are known for example from the "Encyclopedia of Medical Radiology" Vol. 1, part 2 (1965), pages 203 to 212, wherein tomograms are produced with X-rays or similarly penetrating radiation by scanning of the subject under examination with a beam of rays emanating from a source and wherein the beam which issues from the subject under examination acts upon a recording device, the source and recording device being moved in unison to bring about the scanning of the desired bodily layer.

In the known apparatus for producing fluoroscopic tomograms with X-rays or similarly penetrating radiation, at least one element from the group: radiation source, examination subject, and recording device, is moved. Depending upon the methods and recording elements employed, the patient is, as a rule, kept motionless in medical diagnosis. The radiation source is displaced. This requires a great outlay of energy and time also. On the other hand, generally a braking is again necessary at the end of the photographic exposure which likewise demands considerable outlay.

Regarding the method, however, the decisive factor is the process of setting into motion itself, because this enters into the time requirement of the actual photographic exposure. In the case of conventional apparatus for photographing linear layers, 600 milliseconds (600 msec) have been shown to be the shortest photographic times. More rapid photographic sequences (or operating cycles) are possible only with a large outlay. However, in so doing, only a reduction by half of the shortest tomographic photographic times which are otherwise possible can be achieved as a rule. In order to photograph moving organs, such as the heart, tomographic times of 80 msec would have to be obtained. Taking into consideration the movement sequences of individual parts of the heart within the heart-phase, moreover, a tomographic time of 20 msec appears desirable. Rapid movements such as this cannot be obtained with the mechanical means presently available.

SUMMARY OF THE INVENTION

The object which is the basis of the invention consists in disclosing a method and an assembly for the production of tomograms with X-rays or similarly penetrating radiation, with which tomographic times below 80 msec, and preferably at least down to 20 msec can be obtained.

By utilizing a plurality of focal spots, scanning may proceed along a random path which may form a straight line or a curved or meandering line traversing a surface. In the case of focal spots which are arranged in a scan row corresponding to the known path of movement of an X-ray tube for linear tomograms, and which are actuated by the movement of the photographic organ, for example the conventional cassette, the speed of the photograph can be increased. This is based particularly on the fact that neither the heavy photographic subject which, in medical X-ray diagnosis is a photographic person, a patient, nor the radiation source; i.e., an X-ray tube shielded such that it is safeguarded as to radiation, need be set in motion. It suffices to move the lightest element-i.e., the photographic element, such as a film cassette. In an arrangement such as this with a rapidly traveling focal spot, the demand for a short photographic period can also be realized; for example, if, given a path of movement of approximately 40 cm, a larger number of focal spots—for example twenty—are arranged in succession. These focal spots, whose size—approximately $1 \times 1$ to $3 \times 3$ mm, particularly $2 \times 2$ mm—corresponds to the sizes conventional in X-ray diagnosis, can be adjacently disposed on an anode of corresponding length. Actuation can proceed in a conventional fashion in that the cathodes, which are ready for operation, are blocked by a screen (or grid) whose blocking voltage is interrupted during the photographic period. The initiation of this interruption can proceed by means of the moved element as a function of its movement by arranging along its path of movement switches which can be successively actuated by the element, such as magnetic switches, mechanical switches, etc. However, an electronic initiation (or triggering) is also possible in the desired sequence. This is of particular importance during photographing of images with radiation—measuring probes and storage in a data store (or memory). Switching on of the radiators as well as control of the stores are then possible from a central control unit (compare e.g. computer-tomography, U.S. Pat. No. 3,778,614).

In an embodiment in which a special X-ray tube is employed, a straight anode 50 cm in length is provided in a vacuum envelope for photographing linear planar layers. Opposite said anode an array of approximately twenty cathodes is mounted, each of which having a spatial interval from one another of 2.5 cm. A grid (or screen) is connected in series with each cathode, with which grid issuance of the electrons can be blocked. An operating cycle of successive cathode actuation (or switching-on) can thus readily take place in 20 msec or even more rapidly. It is only necessary for switching members to be actuated in synchronism with the photographic assembly, such as the movement of a film cassette, said actuation proceeding along the path of displacement of said photographic assembly. A limit of the speed is given in the case of photographs only by the requirements of advancement of the cassette and the sensitivity of the photographic material. The actuation process can proceed at a random speed. In utilizing a conventional cassette and a known X-ray film, a duration of a photographic exposure of only 20 msec should be obtainable. Electronic image storage is free of this restriction.

Other objects, features and advantages of the invention will be apparent from the following detailed description taken in connection with the accompanying sheet of drawings.

BRIEF DESCRIPTION OF THE DRAWINGS

FIG. 1 illustrates the diagram of a tomographic X-ray assembly designed in accordance with the invention;

FIG. 2 illustrates a basic circuit diagram for realizing the focal spots which can be successively actuated;

FIG. 3 illustrates a section of an X-ray tube comprising an anode opposite which a plurality of cathodes is placed; and FIG. 4 schematically illustrates a non-linear; i.e., a circular, assembly of a plurality of sequentially actuatable radiation sources.

DESCRIPTION OF THE PREFERRED EMBODIMENTS

FIG. 1 illustrates an X-ray apparatus in which a patient support 2 and a radiation source 3 are mounted on a support column 1 in a vertically displaceable fashion. In addition, the electric supply system 4 is provided for the purpose of operation, which is to be supplied with current from the mains. Pursuant to a photographic exposure as defined by the invention, an X-ray tube 5 is set in operation by means of the current supply installation 4, on the one hand, and an X-ray film cassette 6 housed in table 2 in set in motion in the direction of an arrow 7. A focal spot of approximately 2 mm×2 mm ( and having an area of 4 mm$^2$), is thereby produced in the tube, which leads to the production of a cone of rays 8 aand which is moved along a scan path indicated by arrow 10, in a direction opposite to that of the cassette, by means of the sequential actuation of the cathodes referenced with numeral 9.

Switching on of a cathode 9 is synchronized in a simple fashion with the movement of cassette 6 by associating adjacently disposed switches 12 through 16 with the path of movement 11 indicated in FIG. 2 by broken lines. All these switches are closed and are briefly opened only when cassette 6 slides by. One cathode 9 is thereby actuated in each instance, so that one focal spot is obtained on anode 17 traveling in the direction of arrow 10 in steps of 2.5 cm.

Actuation of the focal spots proceeds in a simple fashion by applying a DC voltage 18 from current supply installation 4 in order to produce X-rays between cathode 9 and anode 17, on the one hand. A DC voltage 21 is connected between conductors 19 and 20, on the other hand, said DC voltage bringing cathode 9 to a state of incandescence. In addition, there is disposed between cathode 9 and its associated grid (or screen) 22 through 26, an additional DC voltage 27 which is sufficient to prevent issuance of electrons from 9 onto anode 17. Electrons can impinge on the anode 17 to produce X-rays only when the blocking voltage is disconnected by opening one of the switches 12 throughh 16. Thus, as indicated in FIG. 1, an X-ray beam 8 is produced which is shifted in the direction of arrow 10 to position 8'. A fluoroscopy of movement; i.e., the customary conditions for the tomogram, is thereby achieved.

The embodiment illustrated in FIG. 3 merely represents a possible structural design. In this embodiment, anode 17 is manufactured in the form of a longitudinally extended solid tungsten (W) bar. Oppositely disposed are the cathodes 9 which are helixes or coils, likewise consisting of tungsten wire. The spatial intervals between them are approximately 2.5 cm in each instance. As screens (or grids), iron profiles having a U-shaped cross section are employed in a manner conventional per se in X-ray tubes. On the one hand, they effect a focusing of the electrons being issued from 9 on account of the bevelling on their opening side toward the inside. On the other hand, when a blocking voltage of sufficient magnitude is connected, the screens (or grids) 22 through 26 can prevent impingement of electrons from 9 on anode 17. Given a tube voltage of 100 kilovolts (100 kV) and a focal spot size of 2×2 mm, several hundred volts are sufficient for the blocking voltage. The mode of operation as illustrated in FIG. 2 can thus be achieved.

In FIG. 4 an assembly is illustrated wherein the units consisting of cathodes 9', which are indicated, and non-illustrated blocking screens are arranged in a circle. They have spatial intervals of 5 cm from one another and are spaced from an annularly curved anode 17'. Basically, this assembly corresponds to that of FIGS. 2 and 3. In the latter instance, also, the control of the focal spot actuation is possible by means of mechanical or electronic stepping switches. Operation proceeds as in the case of the assembly according to FIGS. 2 and 3.

In an electronic scanning mode, an array of photodetectors may be arranged to receive transmitted rays from each of the beams such as 8 and 8' in FIG. 1, so that the transmitted rays with respect to each beam position can be electronically evaluated and stored. In this case a central control unit can control sequential actuation of an electronic stepping switch corresponding to switches 12–16, etc., in FIG. 2, and electronically control the storage of the outputs of the photodetectors for each successively actuated beam such as those from 8 to 8' in FIG. 1. With electronic image storage, the time limitations associated with a moving photographic medium are avoided, the stationary array of photodetectors covering the area swept by movement of the photographic medium of cassette 6 in FIG. 1 and providing the desired resolution in the direction of arrow 7 and transversely thereto, and being electronically connected to successive ones of a number of storage arrays, such as twenty, so that the transmitted rays of the succession of twenty beams such as 8 and 8' are electronically recorded.

It will be apparent that many modifications and variations may be effected without departing from the scope of the novel concepts and teachings of the present invention.

I claim as my invention:

1. A tomographic system for producing tomograms of a body with X-rays, said tomographic system comprising X-ray source means for producing X-ray beams for scanning a subject under examination, a recording device for registering the intensity of the X-ray beams which issue from the subject under examination during a scanning operation, said X-ray source means comprising a multiplicity of X-ray beam sources, and scanning means for successive switching-on of the X-ray beam sources to produce the X-ray beams which scan the subject such that a tomographic layer image can be produced with the aid of said recording device, said beam sources being arranged along a scanning path and being consecutively switched on by said scanning means in a selectable sequence and with a duration necessary for actuation of the recording device, means causing said recording device to be aligned with the respective switched on X-ray beam sources so as to receive the consecutively switched on X-ray beams therefrom, said X-ray sources having a vacuum envelope and being formed by an anode within said envelope extending along said scanning path and at least five cathodes within said envelope and disposed in operative relation to successive portions of said anode, and said scanning means comprising a switching grid connected to control emission of electrons from each cathode to the associated portion of the anode, said vacuum envelope comprising a single vacuum envelope, said anode comprising a single elongated anode element in said single vacuum envelope, the successive cathodes being disposed in said single vacuum envelope in adjacent relation to successive portions of said single elongated anode element, and the successive cathodes having a special interval from one another of not more than five centimeters.

2. A tomographic system according to claim 1, characterized in that a photographic film enclosed in a light-proof envelope is utilized as the recording device, with means for moving the photographic film with said movement being synchronous with the consecutive actuation of the successive switching grids to effect tomographic scanning.

3. A tomographic system according to claim 1, characterized in said recording device comprising a measuring probe for converting the X-ray beams into electric measurement results.

4. A tomographic system according to claim 1, characterized in said measuring probe comprising a series of photodetector elements aligned with the respective X-ray sources to receive the respective successively actuated X-ray beams.

* * * * *